United States Patent
Dickerson et al.

(10) Patent No.: US 10,413,314 B2
(45) Date of Patent: Sep. 17, 2019

(54) ULTRASONIC SURGICAL INSTRUMENT WITH ACTIVATION MEMBER PAIR AND SLIDABLE COVER

(71) Applicant: Ethicon Endo-Surgery, LLC, Guaynabo, PR (US)

(72) Inventors: Benjamin D. Dickerson, Cincinnati, OH (US); Brendan J. Oberkircher, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 818 days.

(21) Appl. No.: 14/836,207

(22) Filed: Aug. 26, 2015

(65) Prior Publication Data

US 2017/0056052 A1    Mar. 2, 2017

(51) Int. Cl.
*A61B 17/32*     (2006.01)
*A61B 17/00*     (2006.01)

(52) U.S. Cl.
CPC ........... *A61B 17/320068* (2013.01); *A61B 2017/00017* (2013.01); *A61B 2017/00367* (2013.01); *A61B 2017/00424* (2013.01)

(58) Field of Classification Search
CPC .. A61B 17/320068; A61B 2017/00017; A61B 2017/00367; A61B 2017/00393; A61B 2017/00916; A61B 2017/00946; A61B 2017/00958; A61B 2017/2918
See application file for complete search history.

(56) References Cited

U.S. PATENT DOCUMENTS

| | | |
|---|---|---|
| 5,322,055 A | 6/1994 | Davison et al. |
| 5,324,299 A | 6/1994 | Davison et al. |
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,773,444 B2 | 8/2004 | Messerly |

(Continued)

FOREIGN PATENT DOCUMENTS

| | | |
|---|---|---|
| EP | 1 842 502 A1 | 10/2007 |
| WO | WO 2010/030850 A2 | 3/2010 |

OTHER PUBLICATIONS

U.S. Appl. No. 61/410,603, filed Nov. 5, 2010.

(Continued)

*Primary Examiner* — Diane D Yabut
(74) *Attorney, Agent, or Firm* — Frost Brown Todd LLC

(57) ABSTRACT

An ultrasonic instrument includes a body, an actuation assembly, a shaft assembly, an ultrasonic blade, and a movable member. The body is configured to receive an ultrasonic transducer. The actuation assembly includes a first activation member and a second activation member. The first activation member is operable to trigger activation of the ultrasonic blade in a first power mode. The second activation member is operable to trigger activation of the ultrasonic blade in a second power mode. The movable member is configured to move between a first position and a second position. In the first position, the movable member is configured to permit access to the first activation member and prevent access to the second activation member. In the second position, the movable member is configured to permit access to the second activation member and prevent access to the first activation member.

20 Claims, 8 Drawing Sheets

(56) References Cited

U.S. PATENT DOCUMENTS

| | | |
|---|---|---|
| 6,783,524 B2 | 8/2004 | Anderson et al. |
| 6,945,981 B2 | 9/2005 | Donofrio et al. |
| 8,057,498 B2 | 11/2011 | Robertson |
| 8,152,825 B2 | 4/2012 | Madan et al. |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,393,037 B2 | 7/2016 | Olson et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2014/0163595 A1 | 6/2014 | Witt et al. |
| 2015/0080924 A1 | 3/2015 | Stulen et al. |
| 2015/0148829 A1 | 5/2015 | Kimball et al. |
| 2016/0106455 A1 | 4/2016 | Aldridge et al. |

OTHER PUBLICATIONS

European Examination Report dated Mar. 25, 2019 for Application No. EP 16757449.0, 5 pgs.
International Search Report and Written Opinion dated Nov. 3, 2016 for Application No. PCT/US2016/047349, 11 pgs.

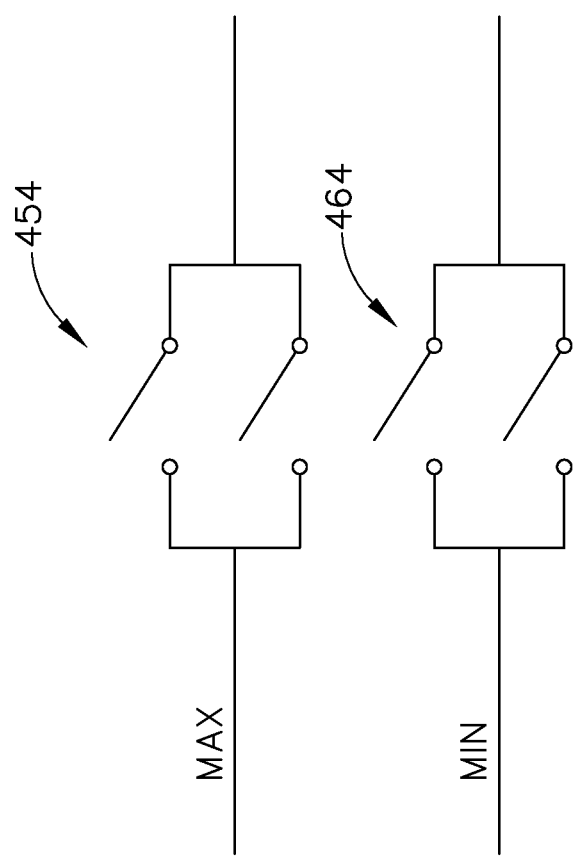

ULTRASONIC SURGICAL INSTRUMENT WITH ACTIVATION MEMBER PAIR AND SLIDABLE COVER

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,831,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts a schematic diagram of an exemplary alternative switch mechanism, suitable for incorporation into the surgical instrument of FIG. 4.

DETAILED DESCRIPTION

I. Overview of Exemplary Ultrasonic Surgical System

Figure 1:
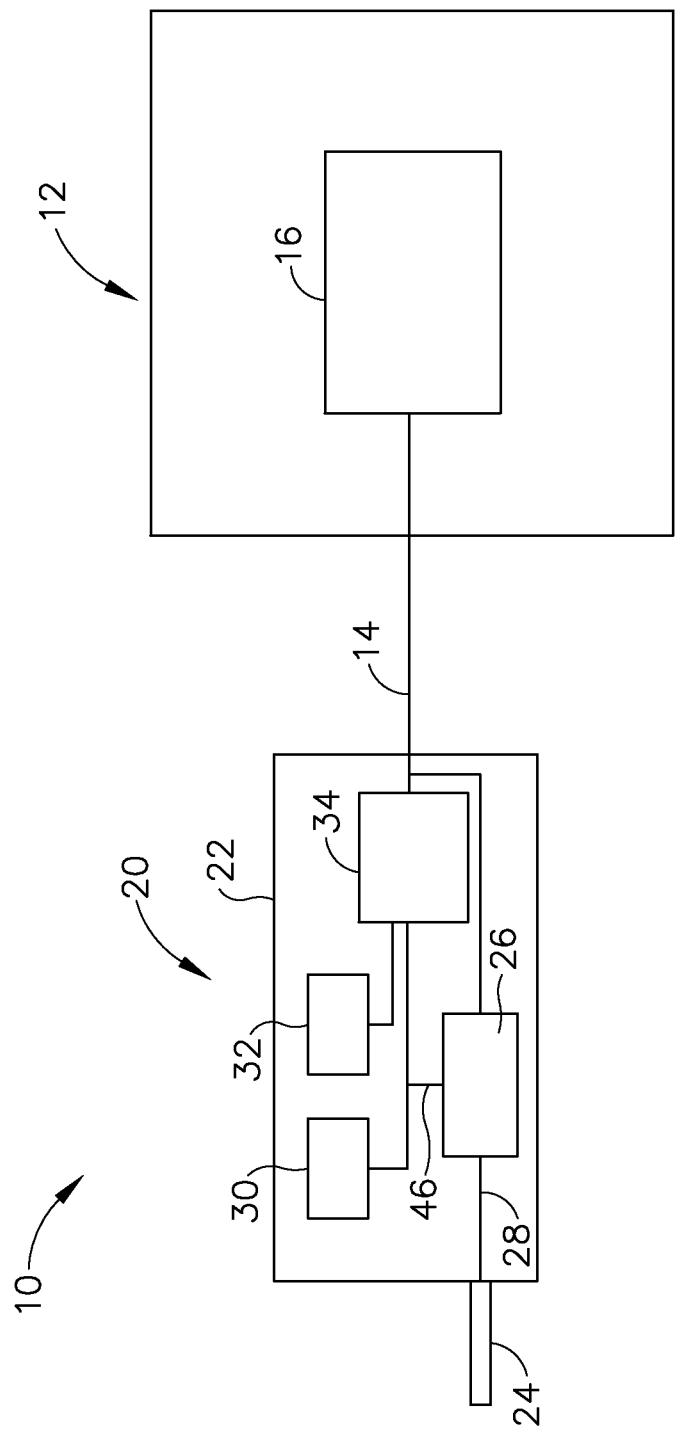
FIG. 1 depicts a block schematic view of an exemplary surgical system.

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. By way of example only, instrument (20) may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,831,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2015/0080924, issued as U.S. Pat. No. 10,172,636 on Jan. 8, 2019; and/or U.S. Pat. App. No. 61/410,603. The disclosures of each of the foregoing patents, publications, and applications are incorporated by reference herein.

It should also be understood that instrument (20) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (20) may have various structural and functional similarities with the devices taught in any of the other references that are cited and incorporated by reference herein. To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (20), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures. It should also be understood that some versions of system (10) may incorporate generator (12) into instrument (20), such that cable (14) may simply be omitted.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (e.g., via remote control, etc.).

In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instruments

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

A. Exemplary Ultrasonic Surgical Scalpel and Scraping Instrument

Figure 2:
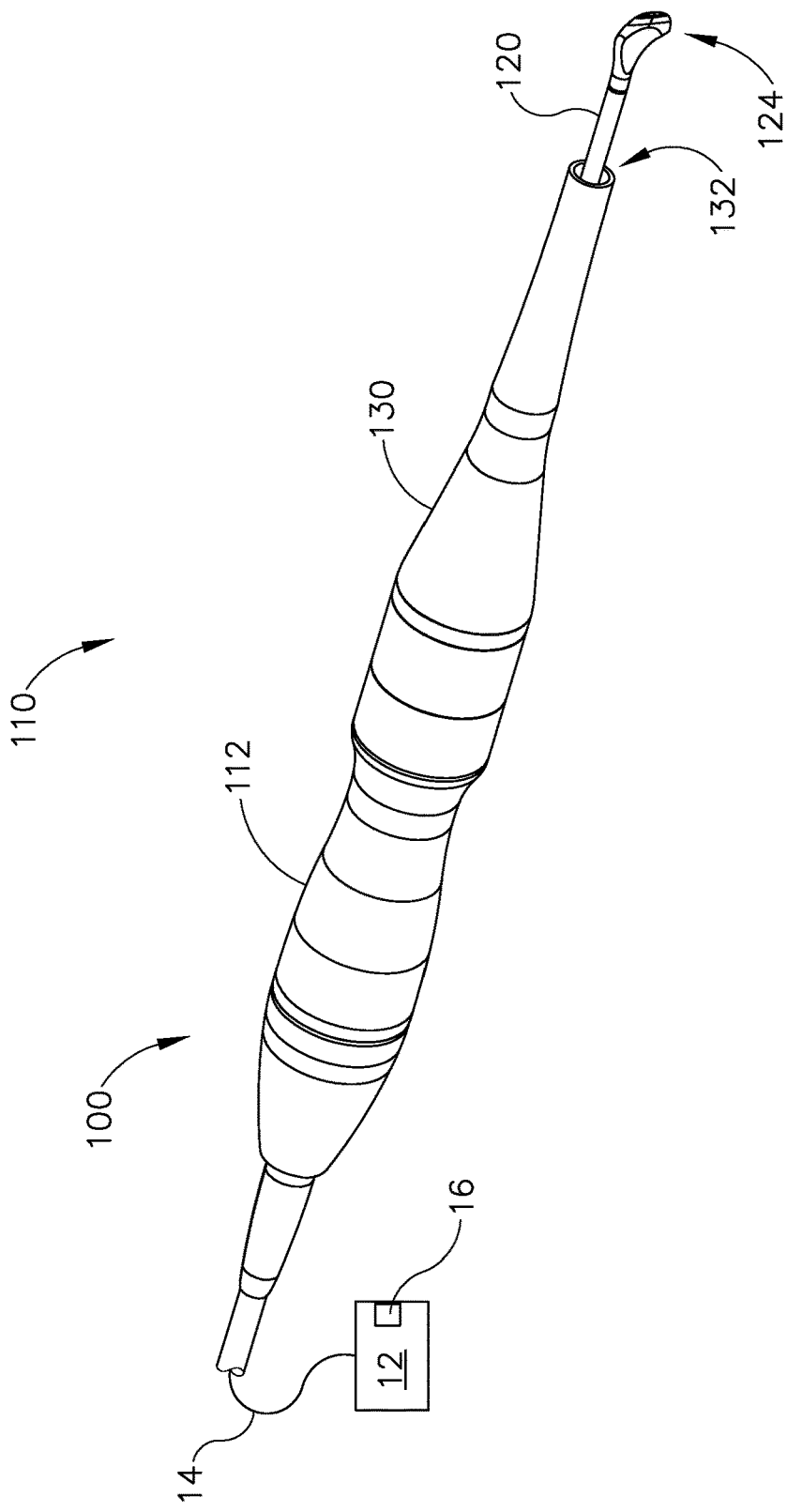
FIG. 2 depicts a perspective view of an exemplary surgical instrument that may be incorporated into the system of FIG. 1.

FIG. 2 illustrates an exemplary ultrasonic surgical instrument (110) that may be used as instrument (20) of system (10) described above. At least part of instrument (110) may therefore be constructed and operable in accordance with at least some of the teachings above with respect to instrument (20). As with instrument (20), instrument (110) is operable to cut tissue and seal or weld tissue (e.g., a blood vessel, etc.) substantially simultaneously. Instrument (110) of this example is configured to be used as a scalpel and/or as a scraping instrument (e.g., like a Cobb elevator instrument).

As shown in FIG. 2, instrument (110) comprises a transducer assembly (100), an acoustic waveguide (120), and a shroud (130). A distal end of waveguide (120) includes an ultrasonic blade (124). Ultrasonic blade (124) of the present example has a scoop-like shape. It should be understood that ultrasonic blade (124) may comprise a curved blade (e.g. Ethicon Endo-Surgery, Inc. Product Code SNGCB), a hook blade (e.g. Ethicon Endo-Surgery, Inc. Product Code SNGHK), a combination hook blade (e.g. Ethicon Endo-Surgery, Inc. Product Code SNGHK2). As yet another merely illustrative example, blade (24) may be constructed in accordance with at least some of the teachings of U.S. Pub. No. 2014/0163595, entitled "Ultrasonic Surgical Blade," published Jun. 12, 2014, issued as U.S. Pat. No. 9,848,900 on Dec. 26, 2017, the disclosure of which is incorporated by reference herein; and/or U.S. Pat. No. 8,057,498, entitled "Ultrasonic Surgical Instrument Blades," issued Nov. 15, 2011, the disclosure of which is incorporated by reference herein. Other suitable configurations that may be used for blade (124) will be apparent to those of ordinary skill in the art in view of the teachings herein.

As will be discussed in more detail below, waveguide (120) is configured to transfer ultrasonic vibrations from transducer assembly (100) to ultrasonic blade (124) to thereby sever and/or seal tissue. A proximal end of shroud (130) threadably couples with a distal end of transducer assembly (100). Shroud (130) defines an interior bore (132) that passes completely through shroud (130) from the proximal end to a distal end thus defining a proximal opening and a distal opening. Waveguide (120) is disposed within interior bore (132) of shroud (130) such that waveguide (120) may be threadably coupled with transducer assembly (100) via the proximal opening of shroud (130). A distal portion of waveguide (120), including ultrasonic blade (124), projects distally from a distal end of shroud (130) via the distal opening of shroud (130).

Transducer assembly (100) of the present example is coupled to a generator (12) via a cable (14), though it should be understood that transducer assembly (100) may instead be a cordless transducer. Transducer assembly (100) may be configured in accordance with the teachings of U.S. Patent Publication No. 2015/0148829, entitled "Methods and Features for Coupling Ultrasonic Surgical Instrument Components Together," published May 28, 2015, issued as U.S. Pat. No. 10,226,271 on Mar. 12, 2019, the disclosure of which is incorporated by reference herein. In the present example, transducer assembly (100) includes a piezoelectric stack (not shown) within transducer housing (112). When transducer assembly (100) of the present example is activated, an electric field is created in the piezoelectric stack, causing the piezoelectric stack and horn (not shown) to oscillate within and relative to housing (112). A mounting flange (not shown) is used to couple a horn (not shown) of transducer assembly (100) to housing (112), to thereby structurally support the piezoelectric stack in housing (112). The mounting flange may be located at a node associated with resonant ultrasonic vibrations communicated from the piezoelectric stack to the horn. Transducer assembly (100) is operable to create mechanical energy, or vibrations, at an ultrasonic frequency (such as 55.5 kHz). If transducer assembly (100) is coupled to waveguide (120) via the horn, then these mechanical oscillations are transmitted through waveguide (120) to ultrasonic blade (124).

Like transducer (26) described above, transducer assembly (100) is coupled with a generator (12) via a cable (14). Transducer assembly (100) receives electrical power from generator (12) and converts that power into ultrasonic vibrations as described above. Generator (12) may include a power source and control module that is configured to provide a power profile to transducer assembly (100) that is particularly suited for the generation of ultrasonic vibrations through transducer assembly (100). By way of example only, generator (12) may comprise a GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (12) may be integrated into instrument (110), and that instrument (110) may even include a battery or other on-board power source such that cable (14) is omitted. Still other suitable forms that generator (12) may take, as well as various features and operabilities that generator (12) may provide, will be apparent to those of ordinary skill in the art in view of the teachings herein.

Ultrasonic vibrations that are generated by transducer assembly (100) are communicated along an acoustic waveguide (120), which extends through shroud (130) to reach ultrasonic blade (124). As noted above, when ultrasonic blade (124) is in an activated state (i.e., vibrating ultrasonically), ultrasonic blade (124) is operable to effectively cut through and seal tissue. It should be understood that waveguide (120) may be configured to amplify mechanical vibrations transmitted through waveguide (120). Furthermore, waveguide (120) may include features operable to control the gain of the longitudinal vibrations along waveguide (120) and/or features to tune waveguide (210) to the resonant frequency of the system.

In the present example, ultrasonic blade (124), being coupled to waveguide (120), oscillates at the ultrasonic frequency. In the present example, the distal end of ultrasonic blade (124) is located at a position corresponding to an anti-node associated with resonant ultrasonic vibrations communicated through waveguide (120), in order to tune the acoustic assembly to a preferred resonant frequency $f_o$ when the acoustic assembly is not loaded by tissue. When transducer assembly (100) is energized, the distal end of ultrasonic blade (124) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz.

When transducer assembly (100) of the present example is activated, the resulting mechanical oscillations are transmitted through waveguide (120) to reach ultrasonic blade (124), thereby providing oscillation of ultrasonic blade (124) at the resonant ultrasonic frequency. Thus, when tissue is contacted by ultrasonic blade (124), the ultrasonic oscillation of ultrasonic blade (124) may simultaneously sever the tissue and denature the proteins in adjacent tissue cells, thereby providing a coagulative effect with relatively little thermal spread. In some versions, an electrical current (e.g., in the RF range) may also be provided through ultrasonic blade (124) to further seal the tissue. For instance, monopolar or bipolar RF energy may be provided through ultrasonic blade (124).

The foregoing components and operabilities of instrument (110) are merely illustrative. Instrument (110) may be configured in numerous other ways as will be apparent to those of ordinary skill in the art in view of the teachings herein. By way of example only, at least part of instrument (110) may be constructed and/or operable in accordance with at least some of the teachings of any of the following, the disclosures of which are all incorporated by reference herein: U.S. Pat. No. 5,322,055; 5,873,873; 5,980,510; 6,325,811; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,831,058 on Jul. 5, 2016; U.S. Pub. No. 2012/0116265, now abandoned; and/or U.S. Pub. No. 2014/0005701, issued as U.S. Pat. No. 9,393,037 on Mar. 24, 2015. Additional merely illustrative variations for instrument (110) will be described in greater detail below. It should be understood that the below described variations may be readily applied to instrument (110) described above and any of the instruments referred to in any of the references that are cited herein, among others.

Figure 3:
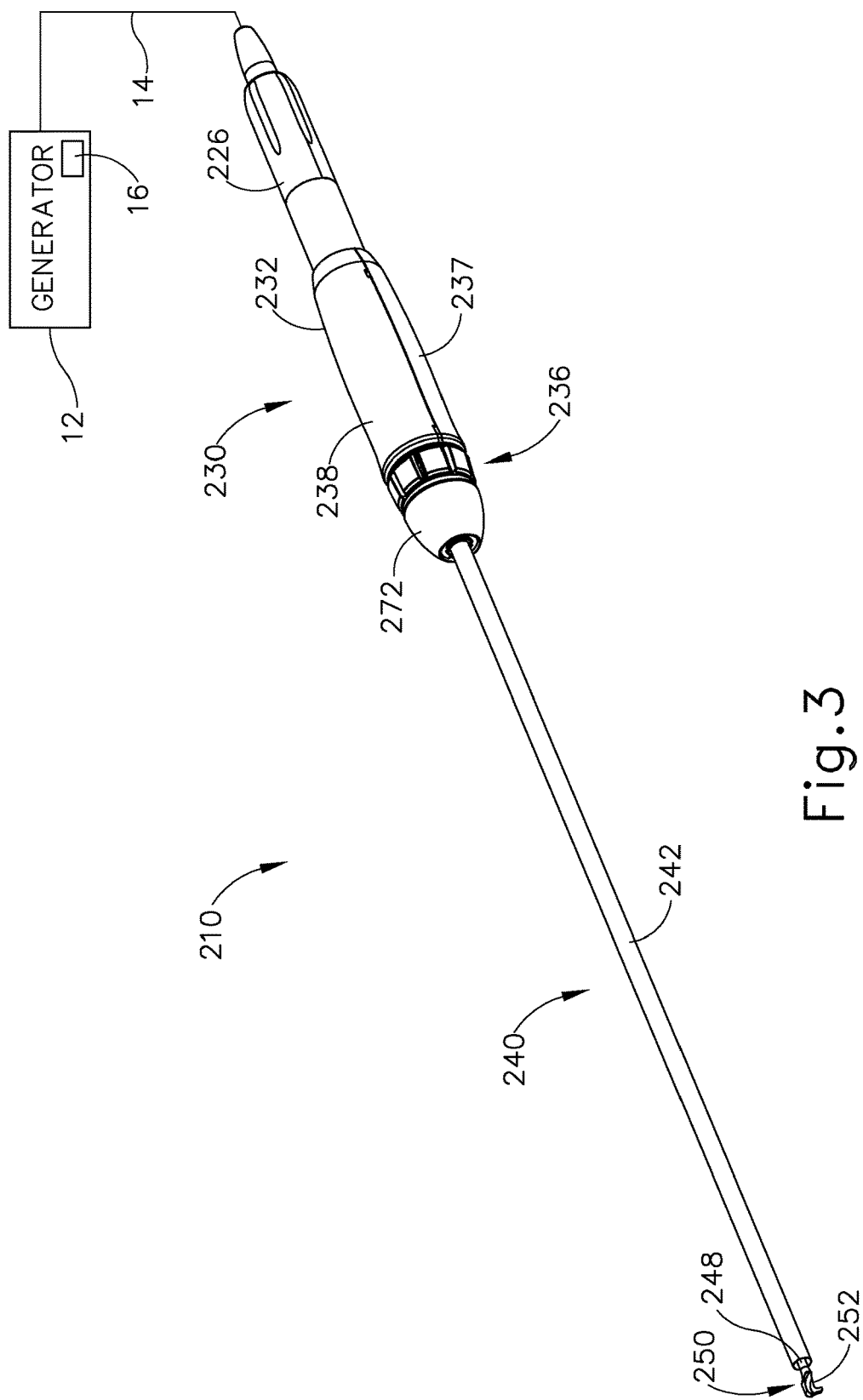
FIG. 3 depicts a perspective view of an exemplary alternative surgical instrument that may be incorporated into the system of FIG. 1.

B. Exemplary Ultrasonic Surgical Instrument with Annular Array of Activation Buttons FIG. 3 illustrates another exemplary ultrasonic surgical instrument (210) that may be used as instrument (20) of system (10) described above. At least part of instrument (210) may therefore be constructed and operable in accordance with at least some of the teachings above with respect to instrument (20). As with instrument (20), instrument (210) is operable to cut tissue and seal or weld tissue (e.g., a blood vessel, etc.) substantially simultaneously. Instrument (210) of this example is configured to be used as a scalpel. As will be described in greater detail below, instrument (210) provides enhanced access to activation features.

As shown in FIG. 3, instrument (210) comprises a handle assembly (230), a shaft assembly (240), and an end effector (250). The proximal end of instrument (210) receives and is fitted with an ultrasonic transducer (226) by insertion of ultrasonic transducer (226) into handle assembly (230). Handle assembly (230) is configured to receive ultrasonic transducer (226) such that ultrasonic transducer (226) may be coupled to a waveguide (248) in shaft assembly (240) by a threaded connection, though any other suitable type of coupling may be used. As shown in FIGS. 2-3, instrument (210) may be coupled with ultrasonic transducer (226) to form a single unit.

Shaft assembly (240) comprises an outer sheath (242) and a waveguide (248) disposed within outer sheath (242). In some versions, outer sheath (242) and a waveguide (248) are sized to fit through a trocar or other minimally invasive access port, such that instrument (210) may be used in a minimally invasive surgical procedure. Waveguide (248) is configured to transmit ultrasonic vibrations from transducer (226) to an ultrasonic blade (252), in a similar manner discussed above with respect to waveguide (28). Waveguide (248) may be flexible, semi-flexible or rigid. Waveguide (248) may also be configured to amplify the mechanical vibrations transmitted through waveguide (248) to blade (252). Waveguide (248) may further include at least one bore (not shown) extending therethrough, substantially perpendicular to the longitudinal axis of waveguide (248). The bore may be located at a longitudinal position corresponding to a node associated with ultrasonic vibrations communicated along waveguide (248). The bore may be configured to receive a connector pin (not shown) that connects waveguide (248) to outer sheath (242). Since the connector pin would be located at a nodal position, the pin would not transmit ultrasonic vibrations from waveguide (248) to outer sheath (242); yet the connector pin may still provide a longitudinal and rotational ground for outer sheath (242).

Blade (252) may be integral with ultrasonic waveguide (248) and formed as a single unit. In some versions, blade (252) may be connected to waveguide (248) by a threaded connection, a welded joint, and/or some other coupling feature(s). The distal end of blade (252) is disposed at or near a longitudinal position corresponding to an anti-node associated with ultrasonic vibrations communicated along waveguide (248) and blade (252) in order to tune the acoustic assembly to a preferred resonant frequency $f_o$ when the acoustic assembly is not loaded by tissue. When transducer (226) is energized, the distal end of blade (252) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (252) may also vibrate in the y-axis at about 1 to about 10 percent of the motion in the x-axis. Of course, movement of blade (252) when transducer (226) is energized may alternatively have any other suitable characteristics.

Handle assembly (230) comprises a tubular elongate body (232) including a plurality of buttons (236). Elongate body (232) is configured to permit a user to grip handle assembly (230) from a variety of positions. By way of example only, handle assembly (230) may be shaped to be grasped and manipulated in a pencil-grip arrangement, in a screwdriver-grip arrangement, and/or in any other suitable fashion. Handle assembly (230) of the present example comprises mating housing portions (237) and (238), though it should be understood that handle assembly (230) may alternatively comprise just a single housing component. Housing portions (237, 238) may be constructed from a durable plastic, such as polycarbonate or a liquid crystal polymer. It is also contemplated that housing portions (237, 238) may alternatively be made from a variety of materials or combinations of materials, including but not limited to other plastics, ceramics, and/or metals, etc.

In the present example, body (232) of handle assembly (230) includes a proximal end, a distal end, and a cavity (not shown) extending longitudinally therein. The cavity is configured to accept a switch assembly and an actuation assembly, in a manner similar to the teachings of U.S. patent application Ser. No. 14/515,129, entitled "Activation Features for Ultrasonic Surgical Instrument," filed Oct. 15, 2014, issued as U.S. Pat. No. 9,907,565 on Mar. 6, 2018, the disclosure of which is incorporated by reference herein. The cavity is also configured to receive at least a portion of transducer (226), as noted above. In the cavity, electrical contacts of transducer (226) interface with switch assembly to provide the operator with finger-activated controls on surgical instrument (210). Transducer (226) of the present example includes two conductive rings (not shown) that are securely disposed within the body of transducer (226). By way of example only, such conductive rings and/or other features of transducer (226) may be provided in accordance with at least some of the teachings of U.S. Pat. No. 8,152,825, entitled "Medical Ultrasound System and Handpiece and Methods for Making and Tuning," issued Apr. 10, 2012, the disclosure of which is incorporated by reference herein.

The switch assembly provides an electro-mechanical interface between buttons (236) of handle assembly (230) and generator (12) via transducer (226) such that actuation of any button (236) results in the activation of generator (12), which then activates transducer (226) to generate ultrasonic vibrations. By way of example only, various components of switch assembly may interface with transducer (226) via ring conductors of transducer (226), which are in turn connected to conductors in cable (14) that connects to generator (12). Thus, when a contact switch of the switch assembly is actuated by the depressing of any button (236), generator (12) activates transducer (226) to generate ultrasonic vibrations. Buttons (236) are provided in an annular array in this example, with buttons (236) being angularly spaced from each other equidistantly. Buttons (236) may be constructed and operable in accordance with at least some of the teachings of U.S. patent application Ser. No. 14/515,129, entitled "Activation Features for Ultrasonic Surgical Instrument," filed Oct. 15, 2014, issued as U.S. Pat. No. 9,907,563 on Mar. 6, 2018, the disclosure of which is incorporated by reference herein.

It should be understood that providing buttons (236) in an angular array may enable the operator to actuate one or more buttons (236) (and thereby activate transducer (226) and blade (252)) at various gripping positions about the longitudinal axis of handle assembly (230). In other words, the operator will not need to contort their fingers, hand, wrist, or arm in order to activate transducer (226) and blade (252) from whichever angular orientation the operator happens to be grasping handle assembly (230). This enhanced access to buttons (236) may be particularly useful when blade (252) has an asymmetry, such that engaging tissue with different sides of blade (252) (e.g., with blade (252) oriented at different angular orientations about the longitudinal axis of waveguide (248)) will provide different effects on tissue. The operator will thus not be forced to sacrifice ergonomic comfort in order to selectively achieve various orientations of blade (252) relative to tissue.

C. Exemplary Ultrasonic Surgical Instrument with Sliding Power Mode Selector

As noted above, there may be instances where it is desirable to enable an operator to engage tissue with an ultrasonic blade at various different angular orientations about the longitudinal axis of an ultrasonic waveguide that is coupled with the ultrasonic blade. This may be particularly desirable where the ultrasonic blade has an asymmetry, such the effect that the activated blade has on tissue will vary depending on the angular orientation (about the longitudinal axis of the waveguide) at which the blade engages tissue. In instrument, this functionality is promoted by providing a set of buttons in an annular array. By providing buttons in an annular array, the operator may continue to grasp and manipulate the handle assembly in the same way regardless of the angular orientation (about the longitudinal axis of the waveguide and the handle assembly) at which the handle assembly is positioned in the operator's hand.

Some instances may also call for enabling activation of the transducer and blade at two or more ultrasonic power settings (e.g., where the amplitude, frequency, and/or other ultrasonic vibration parameters are varied). It may therefore be desirable to enable the operator to select among two or more ultrasonic power settings. Continuing with the premise of enhanced ergonomics, it may be further desirable to enable such power selection in the same way regardless of the angular orientation (about the longitudinal axis of the waveguide and the handle assembly) at which the handle assembly is positioned in the operator's hand. In other words, it may be desirable to enable the operator to select from different power settings or modes regardless of the angular orientation at which the operator happens to be grasping the handle assembly at that moment. The below discussion provides one merely illustrative example of how such enhanced power mode selection may be provided. Other examples will be apparent to those of ordinary skill in the art in view of the teachings herein.

Figure 4:
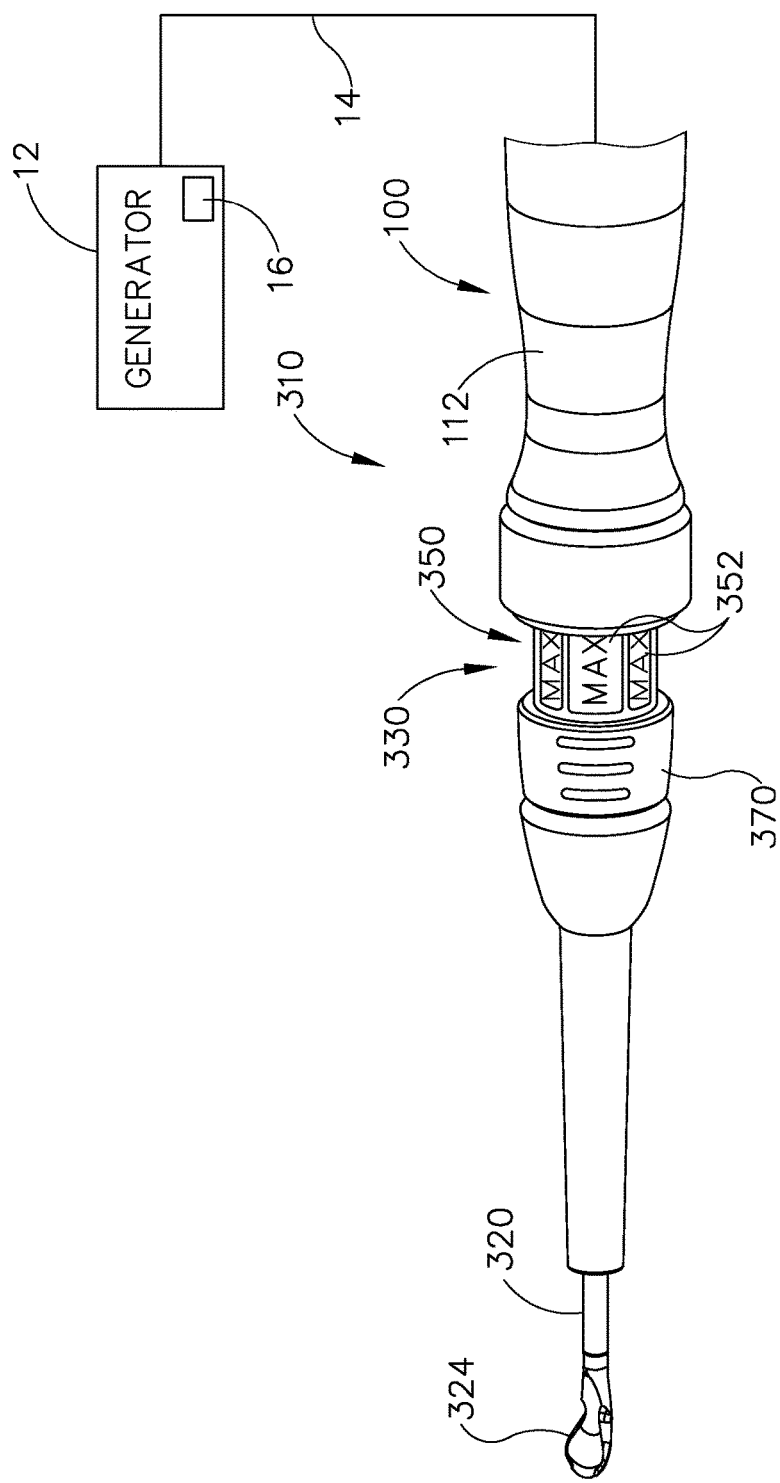
FIG. 4 depicts a perspective view of another exemplary alternative surgical instrument that may be incorporated into the system of FIG. 1, showing a slidable ring thereof in a first position.
Figure 5A:
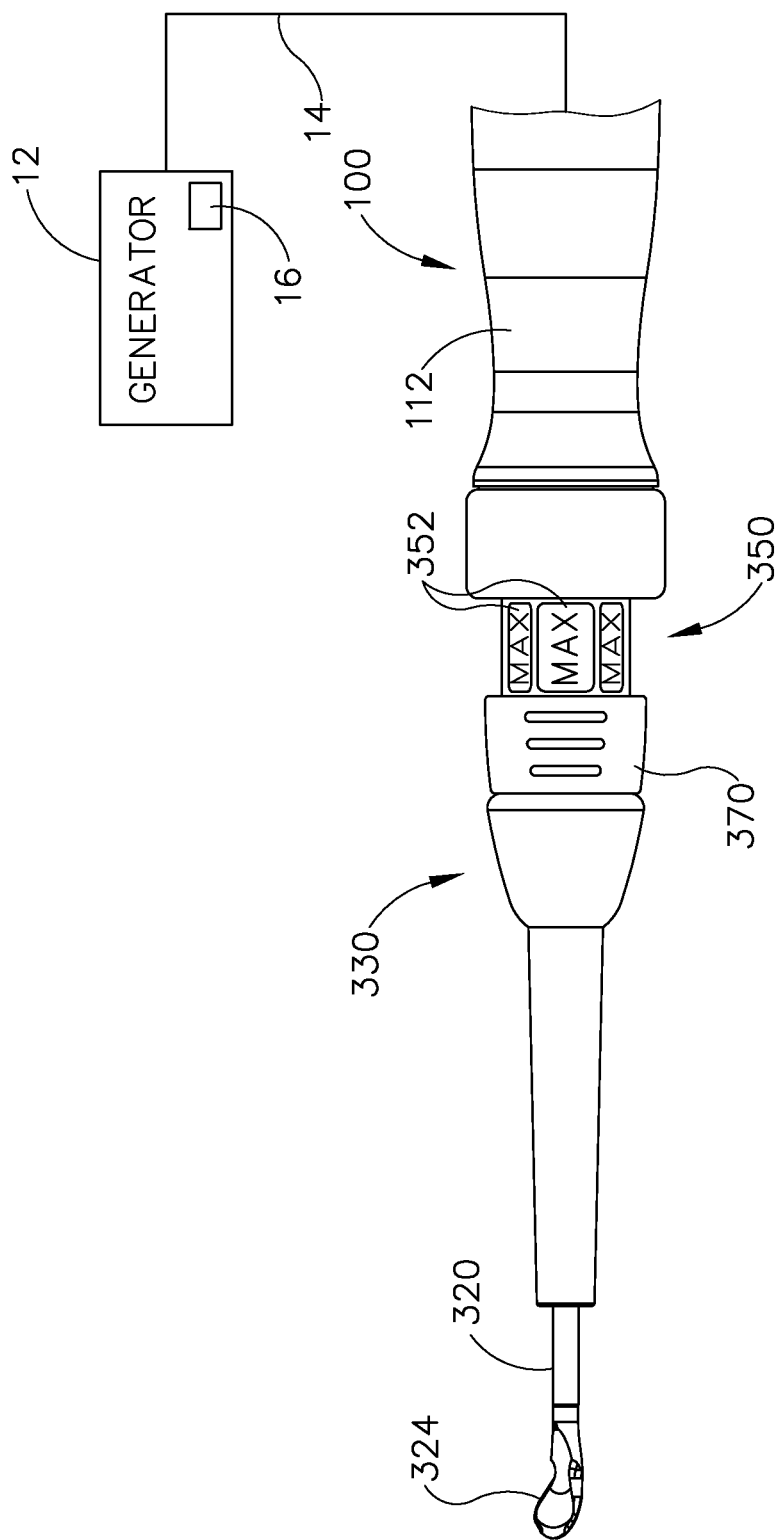
FIG. 5A depicts a side elevational view of the surgical instrument of FIG. 4, showing the slidable ring in the first position.
Figure 5B:
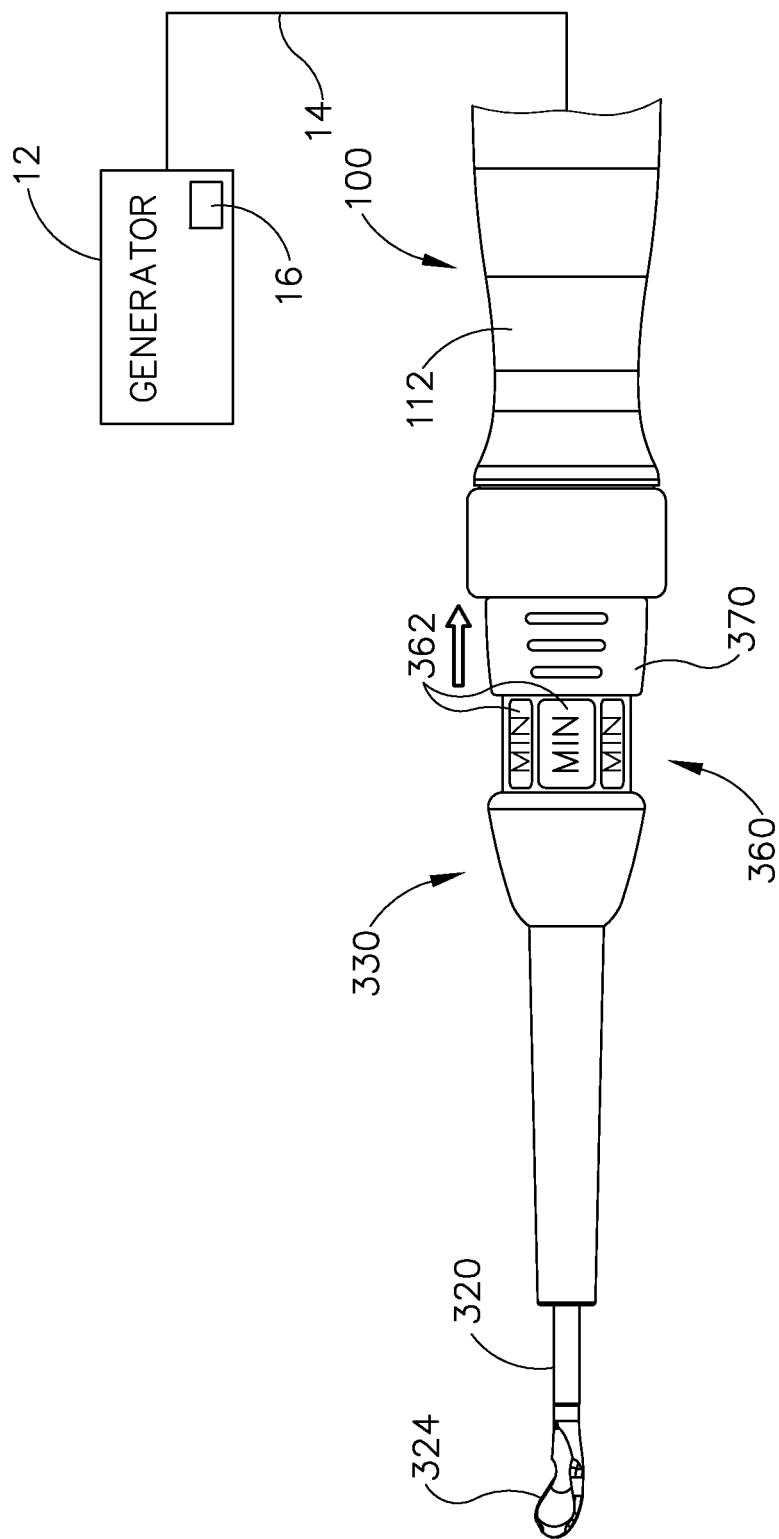
FIG. 5B depicts a side elevational view of the surgical instrument of FIG. 4, showing the slidable ring in a second position.
Figure 6:
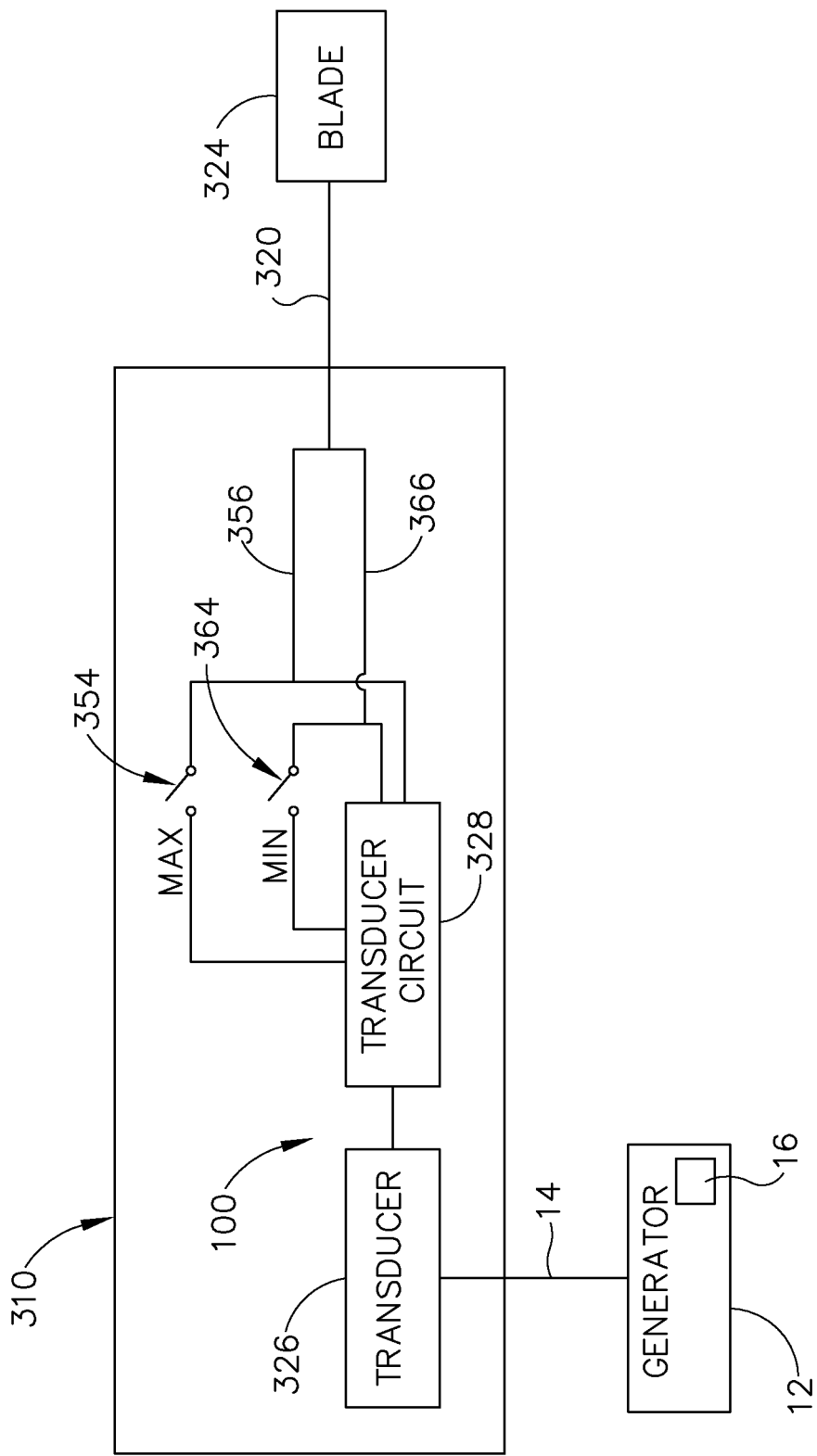
FIG. 6 depicts a block schematic diagram of the surgical instrument of FIG. 4.

FIGS. 4-6 illustrate another exemplary ultrasonic surgical instrument (310) that may be used as instrument (20) of system (10) described above. Except for the differences described below, instrument (310) of the present example has substantial similarities with instrument (110) and with instrument (210). At least part of instrument (310) may therefore be constructed and operable in accordance with at least some of the teachings above with respect to instruments (20, 110, 210). Instrument (310) is operable to cut tissue and seal or weld tissue (e.g., a blood vessel, etc.) substantially simultaneously. Instrument (310) of this example is configured to be used as a scalpel. As will be described in greater detail below, instrument (310) provides enhanced access to activation features and enhanced access to power mode selection features.

As shown in FIGS. 4-5B, instrument (310) of the present example comprises a transducer assembly (100), an acoustic waveguide (320), and shroud assembly (330). A distal end of waveguide (320) includes an ultrasonic blade (324). Ultrasonic blade (324) may be configured just like ultrasonic blade (124) described above. Alternatively, ultrasonic blade (324) may be configured just like ultrasonic blade (252) described above. As yet another alternative, ultrasonic blade (324) may be configured in accordance with any of the other teachings herein and/or in accordance with any of the teachings of any of the various references cited herein. Other suitable configurations that may be used for blade (324) will be apparent to those of ordinary skill in the art in view of the teachings herein.

As will be discussed in more detail below, waveguide (320) is configured to transfer ultrasonic vibrations from transducer assembly (100) to ultrasonic blade (324) to thereby sever and/or seal tissue. A proximal end of shroud (330) threadably couples with a distal end of transducer assembly (100). Shroud (330) defines an interior bore (not shown) that passes completely through shroud (330) from the proximal end to a distal end thus defining a proximal opening and a distal opening. Waveguide (320) is disposed within interior bore of shroud (330) such that waveguide (320) may be threadably coupled with transducer assembly (100) via the proximal opening of shroud (330). A distal portion of waveguide (320), including ultrasonic blade (324), projects distally from a distal end of shroud (330) via the distal opening of shroud (330).

Transducer assembly (100) is substantially similar or identical to transducer assembly (100) discussed above. Particularly, transducer (100) of the present example is coupled to a generator (12) via a cable (14), though it should be understood that transducer assembly (100) may instead be a cordless transducer. Ultrasonic vibrations that are generated by transducer assembly (100) are communicated along an acoustic waveguide (320), which extends through shroud (330) to reach ultrasonic blade (324). As noted above, when ultrasonic blade (324) is in an activated state (i.e., vibrating ultrasonically), ultrasonic blade (324) is operable to effectively cut through and seal tissue. It should be understood that waveguide (320) may be configured to amplify mechanical vibrations transmitted through waveguide (320). Furthermore, waveguide (320) may include features operable to control the gain of the longitudinal vibrations along waveguide (320) and/or features to tune waveguide (20) to the resonant frequency of the system.

Instrument (310) of the present example includes two sets of activators (350, 360), the actuation of which results in activation of transducer (100) and blade (324) at two different ultrasonic power levels or modes. Activator (350) is located proximal to activator (360). Activator (350) comprises an annular array of buttons (352). Activator (360) also comprises an annular array of buttons (362). Each array of buttons (352, 362) may be configured and operable similar to buttons (236) described above. Alternatively, each array of buttons (352, 362) may have any other suitable configuration. For instance, each array of buttons (352, 362) may comprise an array of thin film switches. Other suitable components and configurations that may be used to form each activator (350, 360) will be apparent to those of ordinary skill in the art in view of the teachings herein.

As will be described in greater detail below, activator (350) provides activation of transducer (100) and blade (324) at a relatively low ultrasonic power level; while activator (360) provides activation of transducer (100) and blade (324) at a relatively high ultrasonic power level. To that end, in some examples, when an operator actuates one of buttons (352), the operator's selection is communicated back to control circuitry (16) of generator (12) via cable (14), and control circuitry (16) communicates power from generator (12) according to the low power activation mode. Similarly, if the operator actuates one of buttons (362), the operator's selection is communicated back to control circuitry (16) of generator (12) via cable (14), and control circuitry (16) communicates power from generator (12) according to the high power activation mode. Various ways in which control circuitry (16) may be configured to provide this functionality will be apparent to those of ordinary skill in the art in view of the teachings herein.

Shroud assembly (330) includes a slidable ring (370) that is movable between a first position (FIGS. 4, 5B) and a second position (FIG. 5A) to selectively cover or reveal activators (350, 360). In particular, when slidable ring (370) is in the first position shown in FIGS. 4 and 5B, slidable ring (370) covers activator (350) while activator (360) is left exposed. Thus, when slidable ring (370) is in the first position, the operator may actuate buttons (362) but cannot actuate buttons (352). When slidable ring (370) is in the second position shown in FIG. 5A, slidable ring (370) covers activator (360) while activator (350) is left exposed. Thus, when slidable ring (370) is in the second position, the operator may actuate buttons (352) but cannot actuate buttons (362).

It should be understood from the foregoing that positioning slidable ring (370) in the first position will provide instrument in a "minimum" power mode, where activator (350) will provide activation of transducer (100) and blade (324) at a relatively low ultrasonic power level; while slidable ring (370) in the second position will provide instrument in a "maximum" power mode, where activator (350) will provide activation of transducer (100) and blade (324) at a relatively high ultrasonic power level. Activators (350, 360) may include indicia (e.g., text markings of "MIN" and "MAX", respectively, etc.) to provide visual indication as to which power mode instrument (310) is in. Various suitable forms that indicia may take will be apparent to those of ordinary skill in the art in view of the teachings herein.

As noted above, when slidable ring (370) is in the distal position, instrument (310) is operable with a first level of ultrasonic energy at blade (324); and when slidable ring (370) is in the proximal position, instrument (310) is operable with a second level of ultrasonic energy at blade (324). By way of example only, the first level of energy may be greater than the second level of energy, such that the distal position of slidable ring (370) provides "maximum" power while the proximal position of slidable ring (370) provides "minimum" power. Of course, this is only a merely illustrative, non-limiting example. Those of ordinary skill in the art will immediately recognize that the above-noted relationship may be readily reversed if desired. That is, the first level of energy may be less than the second level of energy, such that the distal position of slidable ring (370) provides "minimum" power while the proximal position of slidable ring (370) provides "maximum" power. It should also be understood that slidable ring (370) may be movable to various other positions between the distal and proximal positions, providing additional power levels to choose from. Moreover, slidable ring (370) may be operable to provide switching between different energy modalities. For instance, slidable ring (370) may be operable to switch between providing ultrasonic energy at blade (324) and providing RF energy at blade (324). Other suitable operational characteristics that may be associated with the different activation modes will be apparent to persons skilled in the art in view of the teachings herein.

In the example shown, slidable ring (370) is fixable in the first and second positions by a locking mechanism such as detent mechanism (not shown). For example, once slidable ring (370) is in the first position, the detent mechanism is configured to maintain slidable ring (370) in the first position absent a sufficient force in the distal direction (towards blade (324)). Similarly, once the slidable ring (370) is in the second position, the detent mechanism is configured to maintain slidable ring (370) in the second position absent a sufficient force in the proximal direction. In other examples, the detent mechanism may be associated with a button or other feature that, when actuated or depressed, releases the detent mechanism and allows slidable ring (370) to move relative to shroud (330). It should be understood that detent features may nevertheless still permit the operator to move slidable ring (370) without requiring the operator to significantly change their grip of instrument (310). For instance, the operator may longitudinally translate slidable ring (370) with just a single finger (e.g., index finger or thumb) while the rest of the operator's fingers remain fixed in position. Various suitable forms that detent features may take will be apparent to those of ordinary skill in the art in view of the teachings herein.

In some examples, slidable ring (370) may be configured such that slidable ring (370) must reside in either the first or second position, such that slidable ring (370) may not reside in an intermediate position between the first and second positions, or in another position that is not the first or second position. In some such examples, slidable ring (370) may be associated with a biasing element that is configured to draw slidable ring (370) into one of the first or second positions, in the event that, for example, an operator fails to fully move slidable ring (370) to the first or second position. However, in other examples, slidable ring (370) may be permitted to reside in a position other than the first and second positions (e.g., that is not associated with any operational mode). For example, slidable ring (370) may reside in a position that is between the first and second positions. As noted above, intermediate positions of slidable ring (370) may correspond with intermediate power modes. As another merely illustrative alternative, slidable ring (370) may render both activators (350, 360) inoperable when slidable ring (370) is located in an intermediate position between the distal and proximal positions. Thus, slidable ring (370) may be considered in an "off" position when slidable ring (370) is located in an intermediate position between the distal and proximal positions.

While instrument (310) of the present example includes two activators (350, 360), in alternative examples, there may be more than two activators (350, 360), such as three or more. In such examples, slidable ring (370) may be configured to allow access to only one activator (350, 360), while preventing access to one or more of the other activator (350, 360). In some such examples, there may be more than one slidable ring (370) to accommodate for additional or alternative configurations of activators (350, 360). Moreover, as shown, each activator (350, 360), includes a respective set of four buttons (352, 362). Alternatively each activator (350, 360) may include a respective set of three or fewer buttons (352, 362); or five or more buttons (352, 362). Moreover, the number of buttons (352) associated with activator (350) may be different from the number of buttons (362) associated with activator (360).

FIG. 6 shows a block schematic diagram of instrument (310). As shown in FIG. 6, instrument (310) includes transducer assembly (100) comprising transducer (326), transducer circuit (328), a first switch (354) associated with first activator (350), and a second switch (364) associated with second activator (360). Instrument (310) further includes a line (356) operably connecting transducer circuit (328) to waveguide (320), and another line (366) operably connecting transducer circuit (328) to waveguide (320). In some examples, switch (354) may be moved to a closed position when slidable ring (370) is in the first position. Then, upon actuation of a button (352), for example, generator (12) communicates power through circuit (328), resulting in ultrasonic energy being delivered to blade (324) according to the first activation mode. Similarly, switch (364) may be moved to a closed position when slidable ring (370) is in the second position. Thus, upon actuation of a button (362), for example, generator (12) communicates power through circuit (328) to waveguide (320), resulting in ultrasonic energy being delivered to blade (324) according to the second activation mode.

In an alternative example, one or both of switches (354, 364) may be configured differently than the manner shown. For example, referring to FIG. 7, alternative switches (454, 464) each include a set of switches, in parallel, that may open and close in a same or different manner than described with respect to switches (354, 364). Other suitable configurations of switches (354, 364, 454, 464) will be apparent to persons skilled in the art in view of the teachings herein. It should also be understood that transducer circuit (328) may be configured in a similar manner to control circuit (34) shown in FIG. 1 and discussed above.

It should be understood from the foregoing that slidable ring (370) may be provided in two different configurations. In one exemplary configuration, slidable ring (370) simply acts as a mechanical shield that selectively covers buttons (352, 362) to thereby prevent buttons (352, 362) from being actuated. For instance, when slidable ring (370) is in a distal position, slidable ring (370) covers buttons (362) and thereby prevents buttons (362) from being actuated; yet provides access to buttons (352) and thereby allows buttons (352) to be actuated. Conversely, when slidable ring (370) is in a proximal position, slidable ring (370) covers buttons (352) and thereby prevents buttons (352) from being actuated; yet provides access to buttons (362) and thereby allows buttons (362) to be actuated. In some such versions where slidable ring (370) simply serves as a mechanical cover that selectively obstructs access to buttons (352, 362), slidable ring (370) does not engage any kind of switches. In such versions, each set of buttons (352, 362) is wired to a respective circuit that enables each set of buttons (352, 362) to activate blade (324) at the corresponding ultrasonic power level. In other words, buttons (352) may be wired to a circuit dedicated to activating blade (324) at a first ultrasonic power level; while buttons (362) may be wired to a separate circuit dedicated to activating blade (324) at a first ultrasonic power level. The longitudinal positioning of slidable ring (370) thus does not affect any electrical circuit configuration—it merely affects accessibility of buttons (352, 362).

However, in another exemplary configuration, slidable ring (370) does in fact actuate switches that select a particular power mode, based on the position at which slidable ring (370) is positioned. In some such versions, when slidable ring (370) is in a distal position, slidable ring (370) closes a switch associated with activation of ultrasonic blade (324) at a first power level. When slidable ring (370) is in a proximal position, slidable ring (370) closes a switch associated with activation of ultrasonic blade (324) at a second power level. In such versions, buttons (352) are not necessarily wired to a circuit that is separate from a circuit that buttons (362) are wired to. If slidable ring (370) were to be removed in some such versions, buttons (352) would activate ultrasonic blade (324) at the same ultrasonic power level as buttons (362). It should therefore be understood that buttons (352) may even be consolidated with buttons (362) into a single set of buttons (rather than being provided as two separate, longitudinally spaced apart sets of buttons (352, 362)), with the consolidated set of buttons being accessible regardless of the longitudinal position of slidable ring (370).

As another variation of this example, the control circuit may include features that are operable to sense the longitudinal position of slidable ring (370), such that the control circuit will select an ultrasonic power level based on the longitudinal position of slidable ring. It should be understood that unlike the previous example where slidable ring (370) merely controls access to buttons (352, 362), the longitudinal positioning of slidable ring (370) in this alternative example does in fact change the electrical circuit configuration, in addition to affecting accessibility of buttons (352, 362).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body, wherein the body defines a longitudinal axis, wherein the body is configured to receive an ultrasonic transducer; (b) an actuation assembly, wherein the actuation assembly comprises: (i) a first activation member, and (ii) a second activation member; (c) a shaft assembly, wherein the shaft assembly comprises an acoustic waveguide; (d) an ultrasonic blade in acoustic communication with the acoustic waveguide, wherein the first activation member is operable to trigger activation of the ultrasonic blade in a first power mode, wherein the second activation member is operable to trigger activation of the ultrasonic blade in a second power mode; and (e) a movable member configured to move between a first position and a second position; wherein the movable member is configured to permit access to the first activation member and prevent access to the second activation member when the movable member is in the first position; wherein the movable member is configured to permit access to the second activation member and prevent access to the first activation member when the movable member is in the second position.

Example 2

The ultrasonic instrument of Example 1, further comprising at least one switch, wherein the at least one switch is in communication with the actuation assembly or the movable member.

Example 3

The ultrasonic instrument of Example 2, wherein the at least one switch comprises a first switch configured to transition from an open state to a closed state in response to actuation of the first activation member.

Example 4

The ultrasonic instrument of Example 3, wherein the at least one switch comprises a second switch configured to transition from an open state to a closed state in response to actuation of the second activation member.

Example 5

The ultrasonic instrument of Example 2, wherein the at least one switch is configured to transition from an open state to a closed state in response to movement of the movable member between the first position and the second position.

Example 6

The ultrasonic instrument of any one or more of Examples 1 through 5, wherein the first activation member comprises a first plurality of buttons.

Example 7

The ultrasonic instrument of Example 6, wherein the first plurality of buttons is arranged in an annular array about the longitudinal axis.

Example 8

The ultrasonic instrument of Example 7, wherein the second activation member comprises a second plurality of buttons.

Example 9

The ultrasonic instrument of Example 8, wherein the second plurality of buttons is arranged in an annular array about the longitudinal axis.

Example 10

The ultrasonic instrument of Example 6, wherein the second activation member comprises a second plurality of buttons.

Example 11

The ultrasonic instrument of Example 10, wherein the second plurality of buttons is positioned distal to the first plurality of buttons.

Example 12

The ultrasonic instrument of any one or more of Examples 1 through 11, wherein the movable member is configured to translate along the body between the first position and the second position.

Example 13

The ultrasonic instrument of any one or more of Examples 1 through 12, wherein the movable member comprises a slidable ring.

Example 14

The ultrasonic instrument of any one or more of Examples 1 through 13, further comprising a first set of detent features configured to selectively retain the movable member in the first position.

Example 15

The ultrasonic instrument of any one or more of Examples 1 through 14, further comprising a second set of detent features configured to selectively retain the movable member in the second position.

Example 16

The ultrasonic instrument of any one or more of Examples 1 through 15, wherein the first power mode provides a higher level of power of ultrasonic vibration than the second power mode, such that the first activation member is operable to trigger activation of the ultrasonic blade at a higher power than the power at which the second activation member is operable to trigger activation of the ultrasonic blade.

Example 17

A handle assembly of an ultrasonic surgical instrument, the handle assembly comprising: (a) a body, wherein the body defines a longitudinal axis, wherein the body is configured to receive an ultrasonic transducer; (b) a shaft assembly, wherein the shaft assembly comprises an acoustic waveguide; (c) an ultrasonic blade in acoustic communication with the acoustic waveguide; (d) an actuation assembly, wherein the actuation assembly comprises: (i) a first plurality of buttons, wherein the plurality of buttons are disposed angularly about the body, (ii) a second plurality of buttons, wherein the second plurality of buttons are disposed angularly about the body, (iii) a first switch operable to enable one or both of the first or second plurality of buttons to trigger activation of the ultrasonic blade at a first power level, and (iv) a second switch operable to enable one or both of the first or second plurality of buttons to trigger activation of the ultrasonic blade at a second power level; and (c) a movable member, wherein the movable member is movable relative to the body between a first position and a second position, wherein the movable member is operable to actuate the first switch in response to positioning of the movable member at the first position, wherein the movable member is operable to actuate the second switch in response to positioning of the movable member at the second position.

Example 18

An ultrasonic instrument comprising: (a) a body, wherein the body defines a longitudinal axis, wherein the body is configured to receive an ultrasonic transducer; (b) an actuation assembly, wherein the actuation assembly comprises: (i) a first annular activation member, and (ii) a second annular activation member; (c) a shaft assembly, wherein the shaft assembly comprises an acoustic waveguide; (d) an ultrasonic blade, wherein the ultrasonic blade is in acoustic communication with the acoustic waveguide, wherein the first annular activation member is operable to activate the ultrasonic blade at a first power level, wherein the second annular activation member is operable to activate the ultrasonic blade at a second power level; and (e) a ring disposed around a portion of the body, wherein the ring is movable along the longitudinal axis between a first position and a second position, wherein the ring is configured to enable the actuation assembly to activate the ultrasonic blade at the first power level in response to positioning of the ring at the first position; wherein the ring is configured to enable the actuation assembly to activate the ultrasonic blade at the second power level in response to positioning of the ring at the second position.

Example 19

The ultrasonic instrument of Example 18, wherein the ring is configured to be fixed in the first position and/or the second position.

Example 20

The ultrasonic instrument of any one or more of Examples 18 through 19, wherein the ring configured to be biased toward the first position and/or the second position.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 5004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
    (a) a body, wherein the body defines a longitudinal axis, wherein the body includes first and second annular recesses that extend along the longitudinal axis, wherein the body is configured to receive an ultrasonic transducer;
    (b) an actuation assembly, wherein the actuation assembly comprises:
        (i) a first activation member disposed within the first annular recess, and
        (ii) a second activation member disposed within the second annular recess;
    (c) a shaft assembly, wherein the shaft assembly comprises an acoustic waveguide;
    (d) an ultrasonic blade in acoustic communication with the acoustic waveguide, wherein the first activation member is operable to trigger activation of the ultrasonic blade in a first power mode, wherein the second activation member is operable to trigger activation of the ultrasonic blade in a second power mode; and
    (e) a movable member configured to move between a first position and a second position;
    wherein the movable member is configured to permit access to the first activation member and prevent access to the second activation member by longitudinally sliding to cover the second annular recess when the movable member is in the first position;
    wherein the movable member is configured to permit access to the second activation member and prevent access to the first activation member by longitudinally sliding to cover the first annular recess when the movable member is in the second position.

2. The ultrasonic instrument of claim 1, further comprising at least one switch, wherein the at least one switch is in communication with the actuation assembly or the movable member.

3. The ultrasonic instrument of claim 2, wherein the at least one switch comprises a first switch configured to transition from an open state to a closed state in response to actuation of the first activation member.

4. The ultrasonic instrument of claim 3, wherein the at least one switch comprises a second switch configured to transition from an open state to a closed state in response to actuation of the second activation member.

5. The ultrasonic instrument of claim 2, wherein the at least one switch is configured to transition from an open state to a closed state in response to movement of the movable member between the first position and the second position.

6. The ultrasonic instrument of claim 1, wherein the first activation member comprises a first plurality of buttons disposed within the first annular recess.

7. The ultrasonic instrument of claim 6, wherein the first plurality of buttons is arranged in an annular array about the longitudinal axis.

8. The ultrasonic instrument of claim 7, wherein the second activation member comprises a second plurality of buttons disposed within the second annular recess.

9. The ultrasonic instrument of claim 8, wherein the second plurality of buttons is arranged in an annular array about the longitudinal axis.

10. The ultrasonic instrument of claim 6, wherein the second activation member comprises a second plurality of buttons.

11. The ultrasonic instrument of claim 10, wherein the second plurality of buttons is positioned distal to the first plurality of buttons.

12. The ultrasonic instrument of claim 1, further comprising a first set of detent features configured to selectively retain the movable member in the first position.

13. The ultrasonic instrument of claim 1, further comprising a second set of detent features configured to selectively retain the movable member in the second position.

14. The ultrasonic instrument of claim 1, wherein when the movable member is located in an intermediate position between the first and second positions, the movable member is configured to render both the first and second activation members inoperable.

15. The ultrasonic instrument of claim 1, wherein at least one of the first or second activation members includes an annular array of at least three spaced apart buttons, wherein the movable member is configured to prevent access to the annular array of the at least three spaced apart buttons in at least one of the first position and second positions.

16. An ultrasonic surgical instrument comprising:
    (a) a body, wherein the body defines a longitudinal axis, wherein the body is configured to receive an ultrasonic transducer;
    (b) a shaft assembly, wherein the shaft assembly comprises an acoustic waveguide;
    (c) an ultrasonic blade in acoustic communication with the acoustic waveguide;
    (d) an actuation assembly, wherein the actuation assembly comprises:
        (i) a first plurality of buttons, wherein the plurality of buttons are disposed angularly about the body,
        (ii) a second plurality of buttons, wherein the second plurality of buttons are disposed angularly about the body, (iii) a first switch operable to enable one or both of the first or second plurality of buttons to trigger activation of the ultrasonic blade at a first power level, wherein the first switch comprises a set of switches in parallel, and (iv) a second switch operable to enable one or both of the first or second plurality of buttons to trigger activation of the ultrasonic blade at a second power level, wherein the second switch comprises a set of switches in parallel; and (e) a movable member, wherein the movable member is movable relative to the body between a first position and a second position, wherein the movable member is operable to actuate the first switch in response to positioning of the movable member at the first position, wherein the movable member is operable to actuate the second switch in response to positioning of the movable member at the second position.

17. An ultrasonic instrument comprising:

(a) a body, wherein the body defines a longitudinal axis, wherein the body is configured to receive an ultrasonic transducer;

(b) an actuation assembly, wherein the actuation assembly comprises:
(i) a first annular activation member, and
(ii) a second annular activation member;

(c) a shaft assembly, wherein the shaft assembly comprises an acoustic waveguide;

(d) an ultrasonic blade, wherein the ultrasonic blade is in acoustic communication with the acoustic waveguide, wherein the first annular activation member is operable to activate the ultrasonic blade at a first power level, wherein the second annular activation member is operable to activate the ultrasonic blade at a second power level; and (e) a ring disposed around a portion of the body, wherein the ring is movable along the longitudinal axis between a first position and a second position, wherein the ring is configured to enable the actuation assembly to automatically activate the ultrasonic blade at the first power level in response to longitudinally moving the entire ring to the first position;

wherein the ring is configured to enable the actuation assembly to automatically activate the ultrasonic blade at the second power level in response to longitudinally moving the entire ring to the second position.

18. The ultrasonic instrument of claim 17, wherein the ring is configured to be fixed in the first position and/or the second position.

19. The ultrasonic instrument of claim 17, wherein the ring configured to be biased toward the first position and/or the second position.

20. The ultrasonic instrument of claim 17, wherein at least one of the first or second annular activation members includes an annular array of at least three spaced apart buttons, wherein the ring is configured to prevent access to the annular array of at least three spaced apart buttons in at least one of the first position and second positions.

* * * * *